United States Patent [19]

Ueda et al.

[11] Patent Number: 5,401,726
[45] Date of Patent: Mar. 28, 1995

[54] 2'METHYLIDENEPYRIMIDINE NUCLEOSIDE COMPOUNDS, THEIR USE AND METHOD FOR PRODUCTION THEREOF

[75] Inventors: Tohru Ueda, Sapporo; Takuma Sasaki, Kanazawa; Akira Matsuda, Sapporo; Keiji Yamagami, Iruma; Akihiro Fujii, Kiyose, all of Japan

[73] Assignees: Yoshitomi Pharaceutical Industries, Ltd., Osaka; Yamasa Shoyu Co., Ltd., Chiba, both of Japan

[21] Appl. No.: 44,039

[22] Filed: Apr. 8, 1993

Related U.S. Application Data

[60] Division of Ser. No. 818,656, Jan. 7, 1992, which is a continuation of Ser. No. 397,656, Aug. 23, 1989, abandoned.

[30] Foreign Application Priority Data

Aug. 25, 1988 [JP] Japan .................................. 212061

[51] Int. Cl.⁶ ............................................. A61K 31/70
[52] U.S. Cl. ..................................... 514/49; 536/28.5; 536/28.52; 536/28.55
[58] Field of Search ............................ 514/49, 50, 51; 536/28.5, 28.52, 28.55

[56] References Cited

U.S. PATENT DOCUMENTS

| | | | |
|---|---|---|---|
| 5,047,520 | 9/1991 | Matsuda et al. | 514/49 |
| 5,183,882 | 2/1993 | Sakata et al. | 514/49 |
| 5,300,636 | 4/1994 | Matsuda et al. | 536/28.5 |

FOREIGN PATENT DOCUMENTS 0310673 4/1989 European Pat. Off. ............ 536/23

OTHER PUBLICATIONS

Takenuki et al., "J. Med. Chem.", 31, 1064–1066 (1988).
"Chemical Abstracts", 110(18) Col. 160409h (1989).
"Chemical and Pharamaceutical Bulletin", 34(4) 1518–1523 (1986).
"Chemical Abstracts", 102(21) Col. 185424g (1985).
"Chemical Abstracts", 104(17) Col. 149328m (1986).

*Primary Examiner*—John W. Rollins
*Assistant Examiner*—James O. Wilson
*Attorney, Agent, or Firm*—Wenderoth, Lind & Ponack

[57] ABSTRACT

2'-Methylidenepyrimidine nucleoside compounds of the general formula:

wherein $R^1$ stands for amino or hydroxy group; $R^2$ stands for a halogen or a lower alkyl when $R^1$ is amino or $R^2$ stands for an alkyl having 2 to 4 carbon atoms, an alkynyl having 2 to 4 carbon atoms or a haloalkyl when $R^1$ is hydroxy group; and $R^3$ stands for hydrogen or a phosphoric acid residue, or salts thereof, compositions containing one or more of these compounds and methods for production of these compounds are disclosed.

Said compounds and salts thereof exhibit noticeable antitumor activities.

1 Claim, No Drawings

2'METHYLIDENEPYRIMIDINE NUCLEOSIDE COMPOUNDS, THEIR USE AND METHOD FOR PRODUCTION THEREOF

This is a divisional of application Ser. No. 07/818,656, filed Jan. 7, 1992, which is a continuation of now abandoned Ser. No. 07/397,656, filed Aug. 23, 1989.

BACKGROUND OF THE INVENTION

This invention relates to novel 2'-methylidenepyrimidine nucleosides possessing an excellent antitumor action, their pharmaceutical use and a method for producing said compounds.

Under the circumstances in which death due to cancer has increased, chemotherapy and immunotherapy in addition to surgical therapy have been widely conducted. In this connection, in chemotherapy, cytosine arabinoside, 5-fluorouracil and the like as antimetabolites, which are considered effective against acute leukemia, have been clinically used. However, the hitherto-known anticancer agents leave much to be desired in respect to therapeutic effect and involve various problems such as side effects. Thus, the development of excellent anticancer agents has been desired in various fields. Under such situations, the present inventors created 2'-deoxy-2'-methylidenecytidine and its pharmaceutically acceptable salts. However, since 2'-deoxy-2'-methylidenecytidine is inferior in solubility and its acid addition salts are unstable, they are unsatisfactory with respect to pharmaceutical production.

SUMMARY OF THE INVENTION

The object of the present invention is to provide novel compounds possessing excellent antitumor action and their pharmaceutical use.

Another object of the present invention is to provide methods for producing said novel compounds.

The present inventors have conducted extensive studies to develop novel compounds useful as an anticancer agent for treating leukemia, lung cancer, gastrointestinal cancer (stomach cancer, colon carcinoma) and melanoma, and having no problems with respect to pharmaceutical production and found that 2'-methylidenepyrimidine nucleoside compounds possesses excellent antitumor action and presents no problems with respect to pharmaceutical production, which culminated in the completion of the present invention.

This invention relates to a 2'-deoxy-2'-methylidenepyrimidine nucleoside compound of the general formula:

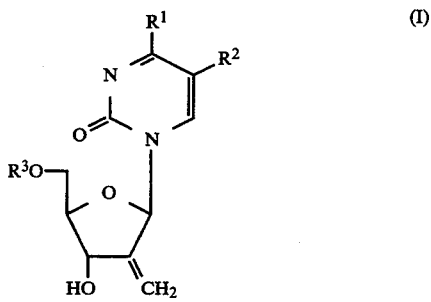

wherein $R^1$ stands for amino or hydroxy group; $R^2$ stands for a halogen or a lower alkyl when $R^1$ is amino or $R^2$ stands for an alkyl having 2 to 4 carbon atoms, an alkynyl having 2 to 4 carbon atoms or a haloalkyl when $R^1$ is hydroxy group; and $R^3$ stands for hydrogen or a phosphoric acid residue, or a salt thereof.

Further, the present invention relates to an anticancer composition for treating leukemia, lung cancer, gastrointestinal cancer (stomach cancer, colon carcinoma) and melanoma, characterized by containing, as the active ingredient, a compound of the general formula (I) or a salt thereof.

Furthermore, the present invention relates to a method for producing compound (I).

In the above-mentioned general formula (I), with reference to $R^2$, the halogen means fluorine, chlorine, bromine or iodine; the lower alkyl means methyl, ethyl, propyl, isopropyl, butyl, isobutyl, tert-butyl or the like; the alkyl having 2 to 4 carbon atoms means ethyl, propyl, isopropyl, butyl, isobutyl, tert-butyl or the like; the alkynyl having 2 to 4 carbon atoms means ethynyl, 1-propynyl, 2-propynyl, 1-butynyl, 2-butynyl, 3-butynyl or the like; and as the halogen of the haloalkyl, mention is made of the halogens as mentioned above and as the alkyl of the haloalkyl, mention is made of the lower alkyls as mentioned above, and such haloalkyls include, for example, trifluoromethyl and chloroethyl.

As the salts of the compounds of the general formula (I), in case where $R^3$ is hydrogen, mention is made of acid addition salts such as hydrochlorides, sulfates, hydrobromides, phosphates, maleates, fumarates, tartrates, succinates, citrates and p-toluenesulfonates, and in case where $R^3$ is a phosphoric acid residue, mention is made of pharmaceutically acceptable salts exemplified by metal salts such as sodium salt, potassium salt, lithium salt, and calcium salt, or ammonium salt.

The present invention encompasses hydrates (1 hydrate, ½ hydrate, ¼ hydrate, 3/2 hydrate) or other solvates of the compounds of the general formula (I) or their salts.

In the case of the compounds of the general formula (I) wherein $R^1$ is hydroxy group, the present invention encompasses the uridine compounds of the general formula:

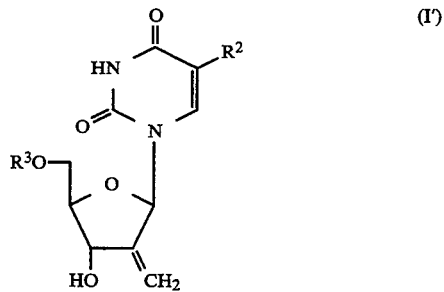

wherein $R^2$ and $R^3$ are of the same meaning as mentioned above, which are the tautomers of the compounds of the general formula (I) wherein $R^1$ is hydroxy group.

As the compound of the general formula (I), there can be mentioned, for example, 2'-deoxy-2'-methylidene-5-fluorocytidine, 2'-deoxy-2'-methylidene-5-chlorocytidine, 2'-deoxy-2'-methylidene-5-bromocytidine, 2'-deoxy-2'-methylidene-5-iodocytidine, 2'-deoxy-2'-methylidene-5-methylcytidine, 2'-deoxy-2'-methylidene-5-ethylcytidine, 2'-deoxy-2'-methylidene-5-ethyluridine, 2'-deoxy-2'-methylidene-5-ethynyluridine or 2'-deoxy-2'-methylidene-5-fluorocytidine-5'-phosphoric acid.

The compounds of the general formula (I) of the present invention wherein $R^1$ is hydroxy group (hereinafter represented as the uridine compounds) can be produced by, for example, the following method:

After the hydroxy groups at the 3'- and 5'-positions of the sugar moiety of a compound of the general formula:

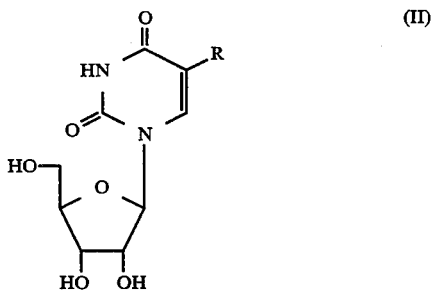

wherein R represents a halogen, an alkyl, an alkynyl having 2 to 4 carbon atoms or a haloalkyl are protected, the hydroxy group at the 2'-position of the sugar moiety is oxidized, followed by reaction with a Wittig reagent to obtain the compound having methylidene at the 2'-position of the sugar moiety and thereafter the protective groups of the hydroxy groups at the 3'- and 5'-positions of the obtained compound are removed, whereafter, if desired, the 5'-position of the sugar moiety is subjected to phosphorylation.

In the above-mentioned reactions, as the protective groups for the hydroxy groups at the 3'- and 5'-positions, any protective groups that are conventionally used as the protective groups for hydroxy groups can be applied. As such protective groups, for example, mention can be made of acyl groups such as acetyl, propionyl, butyryl, benzoyl and naphthoyl; acetal- or ketal-type protective groups such as ethylidene, propylidene, isopropylidene, benzylidene, cyclohexylidene, cyclopentylidene, methoxymethylidene, ethoxymethylidene and dimethoxyethylidene; aralkyl groups such as benzyl, p-methoxybenzyl, 3,4-dimethoxybenzyl, diphenylmethyl, triphenylmethyl, α- or β-naphthylmethyl and α-naphthyldiphenylmethyl; and silyl groups such as trimethylsilyl, t-butyldimethylsilyl, melthyldiisopropylsilyl, triisopropylsilyl and tetraisopropyldisiloxyl (TIPDS).

As the oxidation method for the hydroxy group at the 2'-position, there can be adopted chromic acid oxidation (A method) which comprises using a complex of chromic acid-pyridine-acetic anhydride and the like or activated dimethylsulfoxide oxidation (B method) which comprises using activated dimethylsulfoxide produced from oxalyl chloridedimethylsulfoxide. The oxidation reaction can be carried out in the presence of 1-10 moles of an oxidizing agent relative to 1 mole of the compound to be oxidized at a temperature ranging from −10° C. to room temperature in the case of A method or at a temperature ranging from −10° C. to −80° C. in the case of B method for 1-10 hours.

As the Wittig reagent to be used for the methylidenation reaction, specifically, triphenylphosphinemethylene can be mentioned, and preferably used is a compound which is prepared, immediately before use, from a triphenylphosphonium compound (methyltriphenylphosphonium bromide, methyltriphenylphosphonium iodide, etc.) and a strong alkali (potassium hydride, sodium hydride, n-butyl lithium, sodium amide, etc.) in accordance with the conventional methods. The Wittig reagent can be used suitably in an amount ranging from 1 to 3 times mole relative to 1 mole of the compound. The methylidenation with the use of a Wittig reagent can be carried out by reacting in a solvent (tetrahydrofuran, dioxane, ether, benzene, dimethylsulfoxide, etc., singly or in mixture) at −30° to 30° C. for 0.5 to 20 hours.

The deprotection reaction for the hydroxy groups of the sugar moiety can be conducted by suitably selecting conventional treatment such as acidic hydrolysis, alkaline hydrolysis, ammonium fluoride treatment or catalytic reduction in accordance with the protective group used. For example, when a silyl group is used as the protective group for the hydroxy group, the silyl group can be removed by ammonium fluoride treatment or acidic or alkaline hydrolysis.

The compounds wherein $R^3$ is a phosphoric acid residue can be obtained by reacting with a phosphorylating agent (phosphorus oxychloride, tetrachloropyrophosphoric acid, etc.) which is conventionally used for selective phosphorylation at the 5'-position of nucleosides.

Moreover, the compounds of the present invention of the general formula (I) wherein $R^1$ is amino can be prepared by subjecting a compound to an ordinary amination reaction converting a hydroxy group at the 4-position of the base into an amino group, for example, by reacting a compound having methylidene at the 2'-position of the sugar moiety wherein the hydroxy groups at 3'- and 5'-positions of the sugar moiety are protected, which can be obtained by the above-mentioned method with 1,2,4-triazol in the presence of phosphorus oxychloride and triethylamine to obtain the 4-(1,2,4-triazol-1-yl) compound and converting the obtained compound to the 4-amino compound by passing ammonia gas thereto, followed by the removal reaction of the protective groups for the hydroxy groups and, if desired, phosphorylation.

The reaction with 1,2,4-triazole proceeds under the flow of inert gas such as argon gas in a solvent such as acetonitrile at a temperature ranging from about 0° C. to about room temperature for about 30 minutes to about 5 hours. The ammonia gas is preferably in advance passed through sodium hydroxide. Preferably, the amination reaction with ammonia gas is usually conducted for 1–5 hours.

Among the compounds of the general formula (II) to be used as the starting compounds in the present invention, the compounds of the general formula (II) wherein R is an alkynyl having 2–4 carbon atoms can be produced by, for example, the following method.

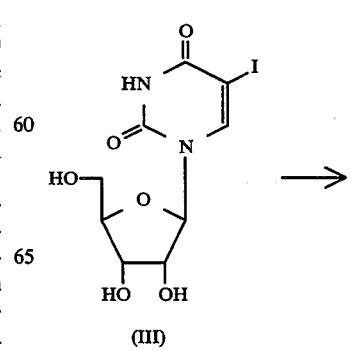

(III)

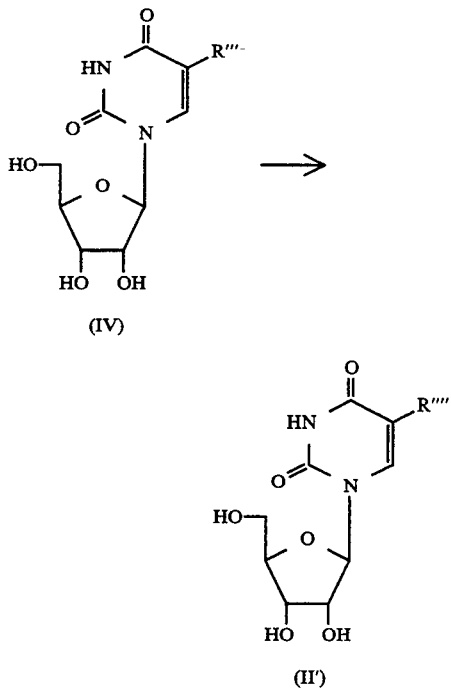

wherein R''' represents an alkynyl having 2 to 4 carbon atoms protected by a silyl group and R'''' represents an alkynyl having 2–4 carbon atoms.

In the above-mentioned reaction, a compound of the general formula (III) is reacted with a metal compound of silyl-protected alkynyl to obtain the compound (IV), followed by the removal reaction of the silyl group to obtain the objective compound (II').

Among the compounds of the general formula (II), the compounds wherein R is an alkyl having 2–4 carbon atoms can be produced by protecting the hydroxy groups at the 3'- and 5'-positions of the sugar moiety of the general formula (II') in accordance with the above-mentioned method and subjecting the protected compound to reduction reaction of the protected compound, followed by the removal of the protective groups of the hydroxy groups at the 3'- and 5'-positions of the sugar moiety.

When the compound of the present invention of the general formula (I) wherein $R^2$ is an alkyl having 2–4 carbon atoms is produced, without the removal of the hydroxy groups at the 3'- and 5'-positions of the sugar moiety of the above-mentioned reductive compounds, the compound having methylidene at the 2'-position of the sugar moiety is obtained in accordance with the methylidination hereinbefore mentioned, whereafter the protective groups are removed, followed by, if desired, phosphorylation at the 5'-position of the sugar moiety.

The objective compounds and synthetic intermediate compounds of the present invention can be isolated and purified by conventional purification and isolation methods (e.g. various chromatography method, ion exchange and adsorption chromatography, recrystallization, etc.) suitably in combination. Specifically, for example, in the case of the nucleoside compounds, after the solvent is distilled off, they are, if necessary, subjected to column chromatography and crystallized from a suitable organic solvent. In the case of nucleotide compounds (wherein $R^3$ is a phosphoric acid residue), they are purified by ion exchange chromatography with ion exchange resin, etc., adsorption column chromatography with activated charcoal, etc. or so on and lyophilization or crystallization to obtain the objective or intermediate compounds in the free acid form, or, if desired, as the salts.

The thus-obtained compounds of the general formula (I) can be converted into the above-mentioned acid addition salts, metal salts or ammonium salts.

Since the compounds of the present invention exhibit remarkable multiplication-suppressive actions against tumor cells and have low toxicity, the pharmaceuticals of the present invention containing them as the active ingredient are useful as anticancer agents for treating leukemia, lung cancer, gastrointestinal cancer (stomach cancer, colon carcinoma) and melanoma. The anticancer compositions of the present invention can be in forms such as powders, granules, tablets, sugar-coated tablets, capsules, syrups, suppositories, medicines for external use, injections and medicines for instillation in a mixture of an effective amount of the compound (I) and pharmaceutically acceptable carriers, excipients, diluents and the like.

While 2'-deoxy-2'-methylidenecytidine is not soluble in saline at the concentration of 25 mg/ml at room temperature, the compound of Example 1 is easily soluble under the same conditions.

The anticancer compositions of the present invention for treating leukemia, lung cancer, gastrointestinal cancer (stomach cancer, colon carcinoma) and melanoma, can be orally or non-orally administered to mammals including humans. Any dosage is preferable so long as the compounds can inhibit the objective cancers effectively at the dosage. While the dosage varies depending on the animal to be treated, the kind of the cancer, the administration route, the composition form and the like, the daily dosage is generally 10–400 mg/kg body weight, preferably 50–200 mg/kg body weight, in the case of medicine for oral administration and 1–20 mg/kg body weight, preferably 1–5 mg/kg body weight, in the case of injections. The administration frequency can be suitably selected in the range from once to 4 times a day.

The anticancer compositions of the present invention for treating leukemia, lung cancer, gastrointestinal cancer (stomach cancer, colon carcinoma) and melanoma, can be used in combination with the other anticancer agents, immunostimulant or other acceptable medicaments.

PREFERED EMBODIMENTS

The invention will be hereinbelow described more specifically by may of examples, but should not be construed as limiting its scope to them.

Example 1

(1) 5-Fluorouridine, 2.62 g, was dissolved in 30 ml of pyridine, 3.3 ml of 1,3-dichloro-1,1,3,3-tetraisopropyldisiloxane was added at 0° C., and the mixture was stirred at 0° C. for 2 hours and then at room temperature for 1.5 hours. By adding 5 ml of water, the solvent was distilled off under reduced pressure. After 100 ml of ethyl acetate and 100 ml of water were added to partition the solution, the organic layer was washed with water twice and then, dried over sodium sulphate and the solvent was distilled off under reduced pressure. The residue was packed into a silica gel column (diameter, 2.4×23 cm) and eluted with 25% ethyl acetate/hexane to afford 3',5'-0-tetraisopropyldisiloxanyl-5-flurouridine as a syrupy substance.

Yield: 4.24 g, 83.9%; Mass (m/z): 504(M+), 461(M+-isopropyl)

(2) The compound obtained in (1) above, 5 g, was dissolved in 10 ml of methylene chloride and mixed with 4 equivalents of chromic acid complex (4 g of chromium oxide, 6.67 ml of pyridine, and 4 ml of acetic anhydride in 100 ml of methylene chloride). The mixture was stirred at room temperature for 1 hour and added dropwise to 500 ml of ethyl acetate and the solution was filtered through a silica gel filter (diameter, 6.0×1.5 cm). The filtrate was distilled off under reduced pressure and the residue was partitioned by 200 ml of ethyl acetate and 200 ml of water. The organic layer was washed with water, dried over sodium sulphate, and the solvent was distilled off under reduced pressure. The residue was placed into a silica gel column (diameter, 2.4×28 cm), eluted with 20% ethyl acetate/hexane, and crystallized from hexane to give 3',5'-0-tetraisopropyldisiloxanyl-2'-oxo-5-fluorouridine.

Yield: 4.3 g, 86%; M.p. 183°–186° C.; Mass(m/z): 502(M+)

Elementary analysis: for $C_{21}H_{35}N_2O_7FSi_2$: Calculated: C, 50.17; H, 7.02; N, 5.57. Found: C, 50.29; H, 7.33; N, 5.58.

(3) Methyltriphenylphosphonium bromide, 8.57 g, was suspended in 80 ml of tetrahydrofuran under argon gas stream, 15.1 ml of n-butyllithium (1.58 mol/μl hexane solution) was added dropwise at 0° C., and the mixture was stirred at room temperature for 1 hour. A solution of 3.02 g of the compound obtained in (2) above in 25 ml of tetrahydrofuran was added dropwise under argon gas stream at 0° C. After 20 minutes, the temperature was restored to room temperature, at which stirring was continued for 3 hours. Neutralization was conducted with 1N ammonium bromide and the solution was concentrated. The solution was partitioned with 100 ml of ethyl acetate and 100 ml of water, and the organic layer was washed with water, dried over sodium sulphate and distilled off under diminished pressure. The residue was placed into a silica gel column (diameter, 3.5×18 cm) and eluted with 20% ethyl acetate/hexane to afford a syrupy product of 3',5'-0-tetraisopropyldisiloxanyl-2'-deoxy-2'-methylidene-5-fluorouridine.

Yield: 2.43 g, 81%; Mass(m/z): 500(M+)

(4) Triethylamine, 1.4 ml, and 684 mg of 1,2,4-triazole were dissolved in 10 ml of acetonitrile and the solution was cooled under argon gas stream to 0° C. Phosphorus oxychloride, 280 μl, was added dropwise, and the mixture was stirred at room temperature for 1 hour. The precipitate was filtered off, and to the filtrate was added dropwise a solution of 500 mg of the compound obtained in (3) above in 5 ml of acetonitrile. After 3 hours at room temperature, the solution was stirred at 50° C. for 1 hour and ammonia gas which had been passed over sodium hydroxide was passed through for 4 hours. The solution was partitioned with 100 ml of chloroform and 100 ml of water, and the aqueous layer was washed with chloroform twice. The collected chloroform layer was dried over sodium sulphate and distilled off under diminished pressure. The residue was placed on a column of silica gel (diameter, 3.5×14 cm) and eluted with 5% ethanol/chloroform to give 3',5'-0-tetraisopropyldisiloxanyl-2'-deoxy-2'-methylidene-5-fluorocytidine as a syrupy substance.

Yield: 435 mg, 87%; Mass(m/z): 499(M+)

(5) The compound obtained in (4) above, 400 mg, was dissolved in 10 ml of tetrahydrofuran, 1.8 ml of tetra-n-butylammonium floride was added, and the mixture was stirred at room temperature for 30 minutes. After neutralization with acetic acid, the solvent was distilled off under reduced pressure. The residue was packed into a silica gel column (diameter, 2.4×18 cm), eluted with ethanol/chloroform, and crystallized from ethanol/ethyl acetate to give 2'-deoxy-2'-methylidene-5-fluorocytidine.

Yield: 177 mg, 86.2%; M.p. 185°–187° C.; Mass(m/z): 257(M+)

Elementary analysis: for $C_{10}H_{12}N_3O_4F$: Calculated: C, 46.70; H, 4.70; N, 16.34. Found: C, 46.06; H, 4.67; N, 16.00.

Example 2

(1) A 1.4 ml quantity of triethylamine and 684 mg of 1,2,4-triazole were dissolved in 10 ml of acetonitrile and the solution was cooled under argon gas stream to 0° C. Phosphorus oxychlorie, 280 μl, was added by drops and the mixture was stirred at room temperature for 1 hour. The precipitate was filtered off, and to the filtrate was added dropwise a solution of 498 mg of 3',5'-0-tetraisopropyldisiloxanyl-2'-methylidenethymidine obtained from thymidine in a similar procedure to Example 1 (1) to (3). After 3 hours, ammonia gas which had been passed over sodium hydroxide was passed through. After 3 hours, 100 ml of chloroform and 100 ml of water were added for partitioning and the resulting aqueous layer was washed with chloroform twice. The collected chloroform layer was dried over sodium sulphate and distilled off under reduced pressure. The residue was placed into a silica gel column (diameter, 3.5×12 cm) and eluted with 5% ethanol/chloroform to give 3',5'-0-tetraisopropyldisiloxanyl-2'-deoxy-2'-methylidene-5-methylcytidine as a syrupy substance.

Yield: 315 mg, 63.3%; Mass(m/z): 495(M+).

(2) The compound obtained in (1) above, 300 mg, was dissolved in 10 ml of tetrahydrofuran and 1.4 ml of tetra-n-butylammonium fluoride was added, and the mixture was stirred at room temperature for 30 minutes. After neutralization with acetic acid, the solvent was distilled under diminished pressure. The residue was placed into a silica gel column (diameter: 2.4×17 cm), eluted with ethanol/chloroform and crystallized from ethanol/ethyl acetate to give 2'-deoxy-2'-methylidene-5-methylcytidine.

Yield: 137 mg, 89.0%; M.p. 198°–204° C. (decomposition).; Mass(m/z): 253(M+).

Elementary analysis: for $C_{11}H_{15}N_3O_4$: Calculate: C, 52.17; H, 5.97; N, 16.59. Found: C, 52.02; H, 5.99; N, 16.37.

Example 3

(1) 5-Chlorouridine, 10 g, was dissolved in 100 ml of pyridine, and 12.44 ml of 1,3-dichloro-1,1,3,3-tetraisopropyldisiloxane was added at 0° C., and the mixture was stirred for 3 hours. After stirring at room temperature for 2 hours, 5 ml of ethanol was added and the solvent was distilled off under diminished pressure. The residue was partitioned with 200 ml of ethyl acetate and 200 ml of water, and the resulting organic layer was dried over sodium sulphate and distilled off under reduced pressure. The residue was placed into a silica gel column(diameter, 3.0×25 cm) and eluted with 25% ethyl acetate/hexane to give a syrupy product of 3',5'-0-tetraisopropyldisiloxanyl-5-chlorouridine.

Yield: 14.63 g, 78.2%; Mass(m/z): 478(M+-isopropyl).

(2) The compound obtained in (1) above, 5.21 g, was dissolved in 15 ml of methylene chloride and mixed with 4 equivalents of chromic acid complex (4 g of chromium oxide, 6.6 ml of pyridine and 4 ml of acetic anhydride in 100 ml of methylene chloride), and the mixture was stirred for 2 hours. The reaction solution was added dropwise to 400 ml of ethyl acetate and filtered through a silica gel filter (diameter, 6.0×1.0 cm). After the solvent was distilled off under reduced pressure, the residue was placed into a silica gel column (diameter, 2.4×30 cm), eluted with 25% ethyl acetate/hexane, and crystallized from ethyl acetate/hexane to give 3',5'-0-tetraisopropyldisiloxanyl-2'-oxo-5-chlorouridine.

Yield: 3.75 g, 72%; M.p. 199°–201° C.; Mass(m/z): 476(M+-isopropyl).

Elementary analysis: for $C_{21}H_{35}N_2O_7ClSi_2$: Calculated: C, 48.49; H, 6.78; N, 5.39. Found: C, 48.24; H, 7.02; N, 5.18.

(3) Methyltriphenylphosphonium bromide, 5.72 g, was suspended in 50 ml of tetrahydrofuran under argon stream and 10.1 ml of n-butyllithium was added dropwise under ice cooling. At room temperature, the solution was stirred for 1 hour. Then, under cooling at 0° C., a solution of 2.08 g of the compound obtained in (2) above in 10 ml of tetrahydrofuran was added dropwise and after 30 minutes, the temperature was returned to room temperature. After 5 hours, neutralization was conducted with 1N ammonium bromide and the solution was partitioned with 100 ml of ethyl acetate and 100 ml of water. The organic layer was washed with water, dried over sodium sulphate, and distilled off under reduced pressure. The residue was placed into a silica gel column (diameter, 5.0×14 cm) and eluted with 25% ethyl acetate/hexane to give 3',5'-0-tetraisopropyldisiloxanyl-2'-deoxy-2'-methylidene-5-chlorouridine as a foamy product.

Yield: 1.7 mg, 81.7%; Mass(m/z): 517(M+)

(4) A 3 ml quantity of triethylamine and 1.52 g of 1,2,4-triazole were dissolved in 20 ml of acetonitrile under argon stream and cooled with ice. To this was added dropwise 620 μl of phosphorus oxychloride and after 30 minutes, the solution was stirred at room temperature for 30 minutes. After the precipitate was filtered off, 1.04 g of the compound obtained in (3) above was added to the filtrate, and the mixture was stirred at room temperature for 3 hours. Ammonia gas which had been passed over sodium hydroxide was passed through the mixture for 2 hours, and partitioning with 100 ml of chloroform and 100 ml of water was conducted. The aqueous layer was washed with chloroform and the collected chloroform layer was dried over sodium sulphate and distilled off under reduced pressure. The residue was placed into a silica gel column (diamter, 3.5×17 cm), eluted with 75% ethyl acetate/hexane and crystallized from ethyl acetate to give 3',5'-0-tetraisopropyldisiloxanyl-2'-deoxy-2'-methylidene-5-chlorocytidine.

Yield: 944 mg, 90.7%; M.p 108°–111° C.; Mass(m/z): 517(M+).

(5) The compound obtained in (4) above, 900 mg, was dissolved in 10 ml of tetrahydrofuran, 4 ml of tetra-n-butylammonium fluoride was added, and the mixture was stirred at room temperature for 30 minutes. After 5 ml of methanol was added, the solvent was distilled off under reduced pressure. The residue was placed into a silica gel column (diameter, 3.5×12 cm), eluted with 20% ethanol/chloroform and crystallized from ethanol/ethyl acetate to give 2'-deoxy-2'-methylidene-5-chlorocytidine.

Yield: 441 mg, 93.4%; M.p. 168°–170° C.; Mass(m/z): 273(M+).

Example 4

(1) 5-Bromouridine, 3.32 g, was dissolved in 30 ml of pyridine and 3.3 ml of 1,3-dichloro-1,1,3,3-tetraisopropyldisiloxane was added at 0° C., and the mixture was stirred for 2 hours. After returning to room temperature, further stirring was conducted for 1 hour and 40 minutes. Water, 5 ml, was added to distill the solvent off under reduced pressure. After azeotropic distillation with ethanol, the residue was placed into a silica gel column (diameter, 2.4×25 cm) and eluted with 25% ethyl acetate/hexane to give 3',5'-0-tetraisopropyldisiloxanyl-5-bromouridine as a syrupy substance.

Yield: 5.05 g, 89.2%; Mass(m/z): 522(M+-isopropyl).

(2) The compound obtained in (1) above, 3.57 g, was mixed with 4 equivalents of chromic acid complex (2.4 g of chromium oxide, 4 ml of pyridine and 2.4 ml acetic anhydride in 70 ml of methylene chloride) and stirred at room temperature for 40 minutes. The reaction solution was added dropwise to 400 ml of ethyl acetate and the solution was filtered through a silica gel filter (diameter, 6.0×1.0 cm). The filtrate was concentrated, and 150 ml of ethyl acetate and 150 ml of water were added for partitioning. The organic layer was washed with water and dried over sodium sulphate, and the solvent was distilled off under reduced pressure. The residue was placed into a silica gel column (diameter, 5.0×14 cm), eluted with 20% ethyl acetate/hexane and crystallized from ethyl acetate-hexane to give 3',5'-0-tetraisopropyldisiloxanyl-2'-oxo-5-bromouridine.

Yield: 3.01 g, 84.8%; M.p. 204°–205° C.; Mass(m/z): 520(M+-isopropyl).

Elementary analysis; for $C_{21}H_{35}N_2O_7Si_2Br$: Calculated: C, 44.75; H, 6.26; N, 4.97. Found: C, 44.57; H, 6.32; M, 4.92.

(3) Methyltriphenylphosphonium bromide, 5.72 g, was suspended in 50 ml of tetrahydrofuran under argon stream, and 10.1 ml of n-butyllithium was added by drops at 0° C. The temperature was restored to room temperature. One hour thereafter, a solution of 2.25 g of the compound obtained in (2) above in 15 ml of tetrahydrofuran was added dropwise at 0° C. After 3 hours, the temperature was restored to room temperature and the solution was stirred overnight and neutralized with 1N ammonium bromide. The solution was partitioned with 150 ml of ethyl acetate and 150 ml of water. The ethyl acetate layer was washed with water and dried over sodium sulphate, and the solvent was distilled off under diminished pressure. The residue was placed into a silica gel column (diameter, 5.0×14 cm) and eluted with 25% ethylacetate/hexane to give 3',5'-0-tetraisopropyldisiloxanyl-2'-deoxy-2'-methylidene-5-bromouridine as a foamy substance.

Yield: 1.72 g, 76.4%; Mass(m/z): 518(M+-isopropyl).

(4) Into 20 ml of acetonitrile were dissolved 3 ml of triethylamine and 1.52 g of 1,2,4-triazole under argon stream, and the solution was cooled with ice. To this was added dropwise 620 μl of phosphorus oxychloride, and after 30 minutes, the temperature was restored to room temperature. Thirty minutes thereafter, the precipitate was filtered off. To the filtrate was added 1.12 g of the compound of (3) above, and the mixture was stirred at room temperature for 3 hours. Ammonia gas which had been passed over sodium hydroxide was passed through the mixture for 3 hours, and 100 ml of chloroform and 100 ml of water were added to partition the solution. The water layer was washed with chloroform, the combined chloroform layer was dried over sodium sulfate, and the solvent was distilled off under reduced pressure. The residue was placed into a silica gel column (diameter, 3.5×17 cm), eluted with 75% ethyl acetate-hexane and crystallized from ethyl acetate-hexane to give 3',5'-0-tetraisopropyldisiloxanyl-2'-deoxy-2'-methylidene-5-bromocytidine.

Yield: 926 mg, 82.7%; M.p. 169°–171° C.; Mass(m/z): 560(M+).

(5) The compound of (4) above, 900 mg, was dissolved in 10 ml of tetrahydrofuran, 4 ml of tetra-n-butylammonium fluoride was added, and the mixture was stirred at room temperature for 30 minutes. Methanol, 5 ml, was added, and the solvent was distilled off under reduced pressure. The residue was placed into a silica gel column (diameter, 3.5×11 cm), eluted with 20% ethanol/chloroform, and crystallized from ethanol/ethyl acetate to obtain 2'-deoxy-2'-methylidene-5-bromocytidine.

Yield, 518 mg, 102%; M.p. 72°–180° C. (decomposition); Mass(m/z): 318(M+).

Example 5

(1) 5-Iodouridine, 10 g, was dissolved in 100 ml of pyridine, 8.9 ml of 1,3-dichloro-1,1,3,3-tetraisopropyldisiloxane was added at 0° C., and the mixture was stirred for 1.5 hours. The temperature was restored to room temperature. Three hours thereafter, 10 ml of water was added and the solvent was distilled off under reduced pressure. After azeotropic distillation with ethanol, the residue was placed into a silica gel column (diameter, 3.0×30 cm) and eluted with 25% ethtyl acetate/hexane to result in 3',5'-0-tetraisopropyldisiloxanyl-5-iodouridine as a syrupy substance.

Yield, 14.7 g, 89%; Mass(m/z): 612(M+).

(2) The compound acquired in (1) above, 5.62 g, was mixed with 4 equivalents of chromic acid complex (3.55 g of chromium oxide, 5.9 ml of pyridine, and 3.55 ml of acetic anhydride in 100 ml of methylene chloride) and the mixture was stirred at room temperature for 40 minutes. The reaction solution was added by drops to 500 ml of ethyl acetate and filtered through silica gel (diameter, 6.0×15 cm), and the filtrate was distilled off under reduced pressure. The residue was placed into a silica gel column (diameter, 5.0×21 cm) and eluted with 25% ethyl acetate/hexane to give 3',5'-0-tetraisopropyldisiloxanyl-2'-oxo-5-iodouridine.

Yield, 1.72 g, 76.4%; Mass(m/z): 610(M+).

(3) Methyltriphenylphosphonium bromide, 7.94 g, was suspended in 80 ml of tetrahydrofuran under argon stream and 14 ml of n-butyllithium was added by drops at 0° C. The temperature was restored to room temperature. One hour thereafter, while the mixture was cooled to 0° C., a solution of 3.39 g of the compound obtained in (2) above in 15 ml of tetrahydrofuran was added dropwise. After one hour, the temperature was restored to room temperature, stirring was conducted overnight. After neutralization with 1N ammonium bromide and concentration, the solution was partitioned with 200 ml of ethyl acetate and 200 ml of water. The organic layer was dried over sodium sulphate and distilled off under reduced pressure. The residue obtained was placed into a silica gel column (diameter, 5.0×22 cm) and eluted with 20% ethyl acetate/hexane to give 3',5'-0-tetraisopropyldisiloxanyl-2 '-deoxy-2 '-methylidene-5-iodouridine as a syrupy substance.

Yield: 1.6 g, 47.2%; Mass(m/z): 608(M+).

(4) Triethylamine, 1.5 ml, and 760 mg of 1,2,4-triazole were dissolved in 10 ml of acetonitrile under argon gas stream and cooled with ice. Phosphorus oxychloride, 310 μl, was added dropwise and 30 minutes thereafter, the temperature was restored to room temperature. After 30 minutes, the precipitate was filtered off and 321 mg of the compound of (3) above was added to the filtrate, followed by stirring at room temperature. Ammonia gas which had been passed over sodium hydroxide was introduced into the solution for 3 hours, and 50 ml of chloroform and 50 ml of water were added to partition the solution. The aqueous layer was washed with chloroform and the collected organic layer was dried over sodium sulphate and distilled off under reduced pressure. The residue was placed into a silica gel column (diameter, 2.4×20 cm), eluted with 10% ethanol/chloroform and crystallized from ethyl acetate to give 3',5'-0-tetraisopropyldisiloxanyl-2'-deoxy-2'-methylidene-5-iodocytidine.

Yield: 169 mg, 52.7%; M.p. 185°–187° C.; Mass(m/z): 607(M+).

(5) The compound obtained in (4) above, 160 mg, was dissolved in 5 ml of tetrahydrofuran, 1 ml of tetra-n-butylammonium fluoride was added and the mixture was stirred at room temperature for 30 minutes. Methanol, 2 ml, was added and the solvent was distilled off under diminished pressure. The residue was placed into a silica gel column (diameter, 3.5×7.0 cm) and eluted with 20% ethanol/chloroform to give 2'-deoxy-2'-methylidene-5-iodocytidine as a syrupy product.

Yield: 92 mg, 97.3%; M.p. 159°–161° C.; Mass (m/z): 365 (M+).

Example 6

(1) 5-Ethynyluridine, 2.1 g, was dissolved in 50 ml of pyridine, 2.6 ml of 1,3-dichloro-1,1,3,3-tetraisopropyldisiloxane was added under ice cooling, and the mixture was stirred for 3 hours. At room temperature, stirring was conducted overnight, and 5 ml of methanol was added to distill the solvent off at reduced pressure. To the residue were added 100 ml of ethyl acetate and 100 ml of water for partitioning. The organic layer was washed with water twice and dried over sodium sulphate, and the solvent was distilled off under reduced pressure. The residue was placed into a column of silica gel (diameter, 5.0×17 cm) and eluted with 25% ethyl acetate/hexane to give 3',5'-0-tetraisopropyldisiloxanyl-5-ethynyluridine as a foamy product.

Yield: 3.26 g, 82%; Mass (m/z): 510 (M+).

(2) The compound obtained in (1) above, 2.04 g, was mixed with 4 equivalents of chromic acid complex (1.55 g of chromium oxide, 2.57 ml of pyridine, and 1.55 ml of acetic anhydride in 40 ml of methylene chloride) and the mixture was stirred at room temperature for 40 minutes. The reaction solution was added by drops to 200 ml of ethyl acetate and filtered through silica gel (diameter, 6.0×1.0 cm). The filtrate was distilled off at reduced pressure and the residue was partitioned with 100 ml of ethyl acetate and 100 ml of water. The organic layer was washed twice and dried over sodium sulphate, and the solvent was distilled off under reduced pressure. The residue was placed into a silica gel column (diameter, 3.5×15 cm) and eluted with 20% ethyl acetate/hexane to give 3',5'-0-tetraisopropyldisiloxanyl-2'-oxo-5-ethynyluridine as a syrupy substance.

Yield: 1.62 g, 81%; Mass (m/z): 508 (M+).

(3) Methyltriphenylphosphonium bromide, 4.29 g, was suspended in 40 ml of tetrahydrofuran under argon gas stream, and under ice cooling, 7.58 ml of n-butyllithium was added dropwise. At room temperature, the solution was stirred for 1 hour and under ice cooling, a solution of 1.52 g of the compound obtained in (2) above in 10 ml of tetrahydrofuran was added dropwise. After 30 minutes, the temperature was restored to room temperature. Six hours thereafter, neutralization was conducted with 1N ammonium bromide, and 100 ml of ethyl acetate and 100 ml of water were added to partition the solution. The organic layer was washed with water twice and dried over sodium sulphate, and then, the solvent was distilled off under reduced pressure. The residue was placed into a silica gel column (diameter, 3.5×20 cm) and eluted with 20% ethyl acetate/hexane to result in 3',5'-0-tetraisopropyldisiloxanyl-2'-deoxy-2'-methylidene-5-ethynyluridine as a syrupy substance.

Yield: 1.12 g, 74%; Mass (m/z): 506 (M+).

(4) The compound obtained in (3) above, 500 mg, was dissolved in 10 ml of tetrahydrofuran and 2.2 ml of tetra-n-butylammonium fluoride was added, and the mixture was stirred at room temperature for 20 minutes. After neutralization with acetic acid, the solvent was distilled off under reduced pressure. The residue was placed into a silica gel column (diameter, 2.4×18 cm), eluted with 10% ethanol/chloroform, and crystallized from ethanol-hexane to afford 2'-deoxy-2'-methylidene-5-ethynyluridine.

Yield: 230 mg, 87%; M.p. 172°–174° C.; Mass (m/z): 264 (M+).

Example 7

(1) Triethylamine, 1.5 ml, and 760 mg of 1,2,4-triazole were dissolved in 10 ml of acetonitrile under argon gas stream and the solution was cooled with ice. A 310 µl quantity of phosphorus oxychloride was added dropwise and 30 minutes thereafter, the solution was stirred at room temperature for 30 minutes. After the precipitate was filtered off, to the filtrate was added 500 mg of 3',5'-0-tetraisopropyldisiloxanyl-2'-deoxy-2'-methylidene-5-ethynyluridine which was obtained in Example 8 (3), and the mixture was stirred at a room temperature for 3 hours. Ammonia gas which had been passed over sodium hydroxide was passed through for 2 hours, and 80 ml of chloroform and 80 ml of water were added for partitioning. The water layer was washed with chloroform and the collected chloroform layer was dried over sodium sulphate, followed by distillation off under reduced pressure. The residue was placed into a silica gel column (diameter, 3.5×14 cm) and eluted with 75% ethyl acetate/hexane to give 3',5'-0-tetraisopropyldisiloxanyl-2'-deoxy-2'-methylidene-5-ethynylcytidine.

Yield: 310 mg, 62%; Mass (m/z): 505 (M+).

(2) The compound obtained in (1) above, 300 mg, was dissolved in 10 ml of tetrahydrofuran and 1.2 ml of tetra-n-butylammonium fluoride was added, and the mixture was stirred at room temperature for 30 minutes. After 2 ml of methanol was added, the solvent was distilled off under reduced pressure. The residue was placed into a silica gel column (diameter, 2.0×12 cm) and eluted with 20% ethanol/chloroform to result in 2'-deoxy-2'-methylidene-5-ethynylcytidine as a foamy product.

Yield: 9.7 mg, 62%.

Example 8

(1) A 3.8 g quantity of 3',5'-0-tetraisopropyldisiloxanyl-5-ethynyluridine, which was obtained in Example 6 (1) was dissolved in 50 ml of methanol and 100 mg of 10% palladium carbon was suspended to conduct catalytic reduction under a moderate pressure of 20 p.s.i. for 4 hours. The reaction solution was filtered through cerite and the solvent was distilled off under reduced pressure. The residue was placed into a silica gel column (diameter, 3.0×20 cm) and eluted with 33% ethyl acetate/hexane to give 3',5'-0-tetraisopropyldisiloxanyl-5-ethyluridine as a syrupy substance.

Yield: 3.22 mg, 84%; Mass (m/z): 514 (M+).

(2) The compound obtained in (1) above, 3.15 g, was mixed with 4 equivalents of chromic acid complex (2.37 g of chromium oxide, 3.93 ml of pyridine, and 2.37 ml of acetic anhydride in 60 ml of methylene chloride) and the mixture was stirred at room temperature for 50 minutes. The reaction solution was added dropwise to 300 ml of ethyl acetate and filtered through silica gel (diameter, 6.0×10 cm). After the filtrate was concentrated, 100 ml of ethyl acetate and 100 ml of water were added to partition the solution. The organic layer was washed with water twice and dried over sodium sulphate, followed by distillation off under reduced pressure. The residue was placed into a silica gel column (3.5 in diameter×15 cm), eluted with 20% ethyl acetate/hexane and crystallized from ethyl acetate-hexane to give 3',5'-0-tetraisopropyldisiloxanyl-2'-oxo-5-ethyluridine.

Yield: 2.54 g, 80.8%; M.p. 176°–177° C.; Mass (m/z): 512 (M+).

Elementary analysis; for $C_{23}H_{40}N_2O_7Si_2$: Calculated: C, 53.88; H, 7.86; N, 5.46. Found: C, 53.59; H, 8.01; N, 5.56.

(3) Methyltriphenylphosphonium-bromide, 5.72 g, was suspended in 50 ml of tetrahydrofuran under argon gas stream and under ice cooling, 10.1 ml of n-butyllithium was added dropwise. The mixture was stirred at room temperature for an hour. To the mixture was added dropwise the solution of 2.05 g of the compound obtained in (2) above in 15 ml of tetrahydrofuran under ice cooling. After 3 hours, the mixture was stirred at room temperature for 5 hours. The solution was neutralized with 1N ammonium bromide, and 150 ml of ethyl acetate and 150 ml of water were added for partitioning. After washing with water twice, the organic layer was dried over sodium sulphate and distilled off under reduced pressure. The residue was placed into a silica gel column (diameter, 3.5×13 cm), eluted with 20% ethyl acetate/hexane, and crystallized from ethyl acetate-hexane to give 3',5'-0-tetraisopropyldisiloxanyl-2'-deoxy-2'-methylidene-5-ethyluridine.

Yield: 1.70 g, 82.7%; M.p. 153°–155° C.; Mass (m/z): 510 (M+).

Elementary analysis: for $C_{24}H_{42}N_2O_6Si_2$: Calculated: C, 56.44; H, 8.29; N, 5.48. Found: C, 56.67; H 8.41; N, 5.36.

(4) The compound obtained in (3) above, 510 mg, was dissolved in 10 ml of tetrahydrofuran, and 2.2 ml of tetra-n-butylammonium fluoride was added, and the mixture was stirred at room temperature for 30 minutes. After neutralization with acetic acid, the solvent was sistilled off under reduced pressure. The residue was placed into a silica gel column (diameter, 3.0×12 cm), eluted with 6.25% ethanol/chloroform, and crystallized from ethanol-hexane to give 2'-deoxy-2'-methylidene-5-ethyluridine.

Yield: 234 mg, 87.2%; M.p. 137°–139° C.; Mass (m/z): 268 (M+).

Elementary analysis; for $C_{12}H_{16}N_2O_5$: Calculated: C, 53.73; H, 6.01; N, 10.44. Found: C, 53.79; H, 5.89; N, 10.67.

Example 9

(1) A 3 ml quantity of triethylamine and 1.52 g of 1,2,4-triazole were dissolved under argon stream in 20 ml of acetonitrile and cooled with ice. To this was added dropwise 620 µl of phosphorus oxychloride and after 30 minutes, the mixture was stirred at room temperature for 30 minutes. After the precipitate was filtered off, 1.2 g of 3',5'-0-tetraisopropyldisiloxanyl-2'-deoxy-2'-methylidene-5-ethyluridine which was obtained in Example 8 (3) was added to the filtrate and stirred at room temperature for 4 hours. Ammonium gas which was passed over sodium hydroxide was introduced into the solution and then, 100 ml of chloroform and 100 ml of water were added to partition the solution. The aqueous layer was washed with chloroform, and the combined chloroform was dried over sodium sulphate and distilled off under reduced pressure. The residue was placed into a silica gel column (diameter, 3.5×20 cm), eluted with 9% ethanol/chloroform, and crystallized from ethyl acetate/hexane to give 3',5'-0-tetraisopropyldisiloxanyl-2'-deoxy-2'-methylidene-5-ethylcytidine.

Yield: 1.0 g, 83.3%; M.p. 197°–200° C.; Mass (m/z): 509 (M+).

(2) The compound obtained in (1) above, 900 mg, was dissolved in 10 ml of tetrahydrofuran, 4 ml of tetra-n-butylammonium fluoride was added, and the mixture was stirred at room temperature for 30 minutes. After addition of 5 ml of methanol, the solvent was distilled off under reduced pressure. The residue was placed into a silica gel column (diameter, 3.5×10 cm), eluted with 20% ethanol/chloroform, and crystallized from ethanol-ethyl acetate to give 2'-deoxy-2'-methylidene-5-ethylcytidine.

Yield: 402 mg, 85.4%; M.p. 194°–196° C.; Mass (m/z): 267 (M+).

Example 10

2'-Deoxy-2'-methylidene-5-fluorocytidine and phosphorus oxychloride are made to react and treated in a usual manner to give 2'-deoxy-2'-methylidene-5-fluorocytidine-5'-phosphoric acid.

Pharmaceutical Preparation Example 1
Tablets comprising:

| | |
|---|---|
| Compound of Example 1 | 50.0 mg |
| Finely divided cellulose | 25.0 mg |
| Lactose | 49.5 mg |
| Starch | 40.0 mg |
| Talc | 5.0 mg |
| Magnesium stearate | 0.5 mg |

The tablets may be subjected to sugar coating or film coating treatment, if desired, thereby to obtain sugar-coated tablets or film-coated tablets.

Pharmaceutical Preparation Example 2
Capsules encapsulated with the ingredients:

| | |
|---|---|
| Compound of Example 1 | 50.0 mg |
| Lactose | 50.0 mg |
| Starch | 15.0 mg |
| Talc | 5.0 mg |

Pharmaceutical Preparation Example 3
Fine powder comprising:

| | |
|---|---|
| Compound of Example 1 | 10% |
| Lactose | 80% |
| Starch | 10% |

Pharmaceutical Preparation Example 4
Granules comprising:

| | |
|---|---|
| Compound of Example 1 | 10% |
| Lactose | 55% |
| Finely divided cellulose | 20% |
| Starch | 15% |

Pharmaceutical Preparation Example 5

| | |
|---|---|
| Compound of Example 1 | 50.0 mg |
| Glucose | 100.0 mg |

The above ingredients are dissolved in purified water to prepare 2 ml of a injection solution.

Pharmaceutical Preparation Example 6
Suppository comprising:

| | |
|---|---|
| Compound of Example 1 | 100 mg |
| Witepsole *H 15 | 950 mg |
| Witepsole *E 75 | 950 mg |

*Witepsole is a trade name of Witten A-G in West Germany.

Pharmaceutical Preparation Example 7

| | |
|---|---|
| Compound of Example 1 | 2 g |
| Ethyl para-hydroxybenzoate | 0.025 g |
| Propyl para-hydroxybenzoate | 0.015 g |
| Sodium laurylsulphonate | 1.5 g |
| Propylene glycol | 12.0 g |
| Stearyl alcohol | 22.0 g |
| White vaseline | 25.0 g |

The above ingredients are dissolved in purified water to prepare 100.0 g of hydrophilic ointment.

Pharmacological Experiments
Effect of the compounds on in vitro cell growth of various tumor cell lines:

The assay of cytotoxicity is dependent on the cellular reduction of MTT [3'-(4,5-dimethylthiazol-2-yl)-2,5-diphenyltetrazolium bromide] by the mitochondrial dehydrogenase of viable cells to a blue formazan product which can be measured spectrophotometrically. Cell suspension, 100 µl, containing $10^4$ tumor cells with or without test sample was incubated for 72 hr in 5% $CO_2$-95% air at 37° C. in 96 well microculture plates (Falcol 3072). The 10 µl of MTT (5 mg/ml) in saline was added to each culture well and incubated for 4 hr at 37° C. The formazan crystals were solubilized by the addition of 100 µl of 10% SDS/0.01N HCl to each well, and incubated for 24 hr at 37° C. The plates were then read at 570 nm on the plate reader. The percentage of cytotoxicity was calculated from the formula:

$$\text{Cytotoxicity (\%)} = \left[ 1 - \frac{(OD_{570} \text{ nm of test well})}{(OD_{570} \text{ nm of control well})} \right] \times 100$$

2′-Deoxy-2′-methylidene-5-fluorocytidine was dissolved in distilled water, and diluted in RPM1 1640 medium. Tumor cell lines were maintained in RPM1 1640 medium (Nissui Seiyaku Co., Ltd., Tokyo, Japan).

Table 1 below shows effect of 2′-deoxy-2′-methylidene-5-fluorocytidine on the growth of various tumor cell lines. $IC_{50}$ values gave the concentrations showing the 50% cytoxity.

TABLE 1

Effect of 2′-deoxy-2′-methylidene-5-fluorocytidine on the growth of various tumor cell lines

| Tumor cell line and its origin | $IC_{50}$ (μg/ml) |
|---|---|
| L1210/c; mouse leukemia | 0.33 |
| B16; mouse melanoma | 6.9 |
| CCRF-CEM; human T cell leukemia | 0.14 |
| MOLT4; human T cell leukemia | 0.036 |
| U937; human histiocytic leukemia | 0.44 |
| HL60; human promyelocytic leukemia | 0.040 |
| PC13; human lung large cell carcinoma | 1.0 |

We claim:

1. A method of treating a patient having a tumor, which comprises administering to the patient an effective anti-tumor amount of a 2′-methylidenepyrimidine nucleoside selected from the group consisting of (1) a compound of the formula

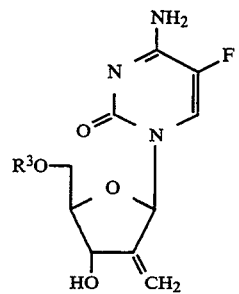

wherein $R^3$ is hydrogen, (2) a salt of said compound and (3) a hydrate of said compound.

* * * * *